United States Patent
Franz et al.

(10) Patent No.: US 10,395,123 B2
(45) Date of Patent: Aug. 27, 2019

(54) METHOD FOR MONITORING A PATIENT WITHIN A MEDICAL MONITORING AREA

(71) Applicant: Drägerwerk AG & Co. KGaA, Lübeck (DE)

(72) Inventors: Frank Franz, Stockelsdorf (DE); Stefan Schlichting, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 0 days.

(21) Appl. No.: 15/029,899

(22) PCT Filed: Oct. 16, 2014

(86) PCT No.: PCT/EP2014/002788
§ 371 (c)(1),
(2) Date: Apr. 15, 2016

(87) PCT Pub. No.: WO2015/055312
PCT Pub. Date: Apr. 23, 2015

(65) Prior Publication Data
US 2016/0267327 A1  Sep. 15, 2016

(30) Foreign Application Priority Data
Oct. 17, 2013  (DE) .......... 10 2013 017 264

(51) Int. Cl.
*G06K 9/00* (2006.01)
*A61B 5/11* (2006.01)
(Continued)

(52) U.S. Cl.
CPC ........ *G06K 9/00771* (2013.01); *A61B 5/0077* (2013.01); *A61B 5/1077* (2013.01);
(Continued)

(58) Field of Classification Search
CPC . A61B 5/1128; A61B 2505/03; A61B 5/0013; A61B 5/002; A61B 5/0033;
(Continued)

(56) References Cited

U.S. PATENT DOCUMENTS

2006/0056655 A1* 3/2006 Wen ............... G06F 19/3418
                                                        382/103
2007/0136102 A1    6/2007 Rodgers
(Continued)

FOREIGN PATENT DOCUMENTS

| DE | 10 2004 024 096 A1 | 7/2005 |
| DE | 11 2011 103 310 T5 | 7/2013 |
| JP | 2004-096 457 A | 3/2004 |

OTHER PUBLICATIONS

Anonymous: "c#—Kinect hand waving gesture—Stack Overflow", Apr. 5, 2012 (Apr. 5, 2012), XP055168773, Retrieved from the Internet: URL:http://stackoverflow.com/questions/9918926/kinect-hand-waving-gesture [retrieved on Feb. 10, 2015] the whole document.

(Continued)

*Primary Examiner* — Bhavesh M Mehta
*Assistant Examiner* — Ian L Lemieux
(74) *Attorney, Agent, or Firm* — McGlew and Tuttle, P.C.

(57) ABSTRACT

A method for monitoring a patient (22a) within a medical monitoring area (100) by means of a monitoring system (200) with a depth camera device (210). The method includes the following steps:
  generating a point cloud (30) of the monitoring area (100) with the monitoring system (200);
  analyzing the point cloud (30) for detecting predefined objects (20), especially persons (22);
  determining a location of at least one detected object (20) in the monitoring area (100); and
(Continued)

comparing the determined location of the at least one detected object (20) with at least one predefined value (40) for the location of this detected object (20).

40 Claims, 6 Drawing Sheets

(51) Int. Cl.
| | |
|---|---|
| *G08B 21/22* | (2006.01) |
| *A61B 5/00* | (2006.01) |
| *A61B 5/107* | (2006.01) |
| *G08B 21/02* | (2006.01) |
| *G08B 25/00* | (2006.01) |

(52) U.S. Cl.
CPC .......... *A61B 5/1079* (2013.01); *A61B 5/1113* (2013.01); *A61B 5/1128* (2013.01); *G08B 21/0263* (2013.01); *G08B 21/22* (2013.01); *A61B 2576/00* (2013.01); *G08B 25/002* (2013.01); *G08B 25/006* (2013.01)

(58) Field of Classification Search
CPC .... A61B 5/1113; A61B 5/1115; A61B 5/1117; A61B 5/112; A61B 5/1123; A61B 5/6889; A61B 5/6892; A61B 5/7445; A61B 5/7475; G08B 21/0476; G08B 21/043; G08B 21/22; G08B 21/245; G06F 3/017; G06K 9/00335; G06K 9/00771; G06K 9/00369; G06Q 50/22
See application file for complete search history.

(56) References Cited

U.S. PATENT DOCUMENTS

| | | | |
|---|---|---|---|
| 2011/0043630 A1 | 2/2011 | McClure et al. | |
| 2011/0316697 A1* | 12/2011 | Krahnstoever | G08B 13/19608 340/540 |
| 2012/0075464 A1 | 3/2012 | Derenne et al. | |
| 2013/0094705 A1* | 4/2013 | Tyagi ................. | G06K 9/00369 382/103 |
| 2013/0182107 A1* | 7/2013 | Anderson ............. | G08B 21/02 348/143 |
| 2014/0056472 A1* | 2/2014 | Gu ..................... | G06K 9/00208 382/103 |
| 2014/0228985 A1* | 8/2014 | Elliott ................... | A63B 71/06 700/91 |

OTHER PUBLICATIONS

René Weller: "A Brief Overview of Collision Detection" In: "New Geometric Data Structures for Collision Detection and Haptics", Jul. 25, 2013 (Jul. 25, 2013), Springer International Publishing, Heidelberg, XP055169735, ISSN: 2192-2977 ISBN: 978-3-31-901020-5 pp. 9-46, DoI: 10.1007/978-3-319-01020-5 2, p. 10, line 21-line 25.

Jan Klein et al: "Point Cloud Collision Detection", Computer Graphics Forum, vol. 23, No. 3, Sep. 1, 2004 (Sep. 1, 2004), pp. 567-576, XP055169738, ISSN: 0167-7055, DoI: 10.1111/j.1467-8659.2004.00788.x the whole document.

Bauer Sebastian et al Li Xue Xueliiotatee Uq Edu Au the University of Queensland School of Information Technology and Electronic E: "Real-Time Range Imaging in Health Care: A Survey", Jan. 1, 1901 (Jan. 1, 1901), Lecture Notes in Computer Science; [Lecture Notes in Computer Science], Springer Verlag, DE, pp. 228-254, XP047220415, ISSN: 0302-9743 ISBN: 978-3-319-10553-6 the whole document.

\* cited by examiner

METHOD FOR MONITORING A PATIENT WITHIN A MEDICAL MONITORING AREA

CROSS REFERENCE TO RELATED APPLICATIONS

This application is a United States National Phase Application of International Application PCT/EP2014/002788 filed Oct. 16, 2014 and claims the benefit of priority under 35 U.S.C. § 119 of German Patent Application 10 2013 017 264.0 filed Oct. 17, 2013 the entire contents of which are incorporated herein by reference.

FIELD OF THE INVENTION

The present invention pertains to a method for monitoring a patient within a medical monitoring area as well as to a monitoring system for carrying out such a method.

BACKGROUND OF THE INVENTION

It is known, in principle, that patients must be subjected to monitoring. For example, the intensity with which the monitoring must be designed depends on the particular medical situation of the patient. It is thus problematic, for example, that confused patients frequently act against medical advice. For example, patients who are provided with a tube and are in a confused mental state tend to remove the tube themselves. In addition, there is a risk that patients who are classified as bedridden leave the bed and are injured. There also is a risk of seizures, so that the patient may additionally become medically compromised. It is extraordinarily labor-intensive to keep the above-mentioned risks under control or to reduce them. For example, a personal monitoring by means of monitoring staff is thus necessary, so that the monitoring person must be present, in the extreme case, in the interior of the patient room all the time. This is associated with very high costs, so that this is actually guaranteed in extremely rare cases only. Another known possibility is to use monitoring cameras, so that a corresponding monitoring person in a monitoring room can monitor a plurality of patients simultaneously by means of the monitors. However, a relatively heavy use of manpower is still necessary in this case as well, because this monitoring must usually be carried out without interruptions 24 hours a day and 7 days a week. In addition, attention of the monitoring person is decisive for the actual risk assessment by the monitoring in case of monitoring a plurality of patients. In particular, inattentiveness or tiredness of the monitoring person leads to an incalculable increase in the risk for the patient. Another drawback is the fact that the private sphere of the patient, relatives or coworkers is compromised.

SUMMARY OF THE INVENTION

An object of the present invention is to at least partially eliminate the above-described drawbacks. An object of the present invention is, in particular, to achieve automation of the monitoring of the patients at least partially in a cost-effective and simple manner and preferably to also make it possible at least to partially automate the documentation and provision of contextual information for other medical devices.

The above object is accomplished by the method according to the invention and by a monitoring system having the features according to the invention. Features and details that are described in connection with the method according to the present invention also apply, of course, in connection with the monitoring system according to the present invention and vice versa, so that reference is or can always mutually be made to the individual aspects of the present invention concerning the disclosure.

A method according to the present invention is used to monitor a patient within a medical monitoring area by means of a monitoring system with a depth camera device. The method according to the present invention has the following steps for this:

a generation of a point cloud of the monitoring area with the monitoring system, analysis of the point cloud to detect predefined objects, especially persons, a determination of the location of at least one detected object in the monitoring area, and a comparison of the determined location of a detected object with at least one predefined value for the location of this detected object.

Consequently, a monitoring method is carried out according to the present invention at least partially in an automated manner. Data information of the monitoring system is accessed in the process. This monitoring system is equipped with a depth camera device, which is capable of making depth information of the monitoring area available. It may be, e.g., a depth camera or a combination of a plurality of depth cameras. A depth camera device according to the present invention or the monitoring system may, of course, also have further, additional sensors, especially sensors of a different type. The core is, however, the possibility of generating a point cloud, for which the depth information of the depth camera device can be made available in a cost-effective and simple manner.

The medical monitoring area is defined especially as a patient room in a hospital. However, other medical institutions may also be monitored with the method according to the present invention. Thus, entire hospital sections, the floors and staircases of the hospital as well as entire hospital wings may be monitored by a method according to the present invention. However, the core of the present invention and also the principal advantages are achieved especially in locally limited monitoring areas, e.g., a floor in a hospital and individual patient MOMS.

The depth camera device is capable of providing depth information. Depending on the quality of the particular depth camera, this happens with different resolutions. The result of such a monitoring with a depth camera device is usually a three-dimensional point cloud. Individual points can be distinguished from one another in terms of their quality and in terms of their local representation. Distances between individual points in space can thus be detected in a three-dimensional manner. If such three-dimensional images are recorded over a rather long time period, a four-dimensional information structure will correspondingly be generated, from which the change in the point cloud can be recognized as a fourth dimension. Interacting with the depth camera device, the monitoring system can perform the analysis. It is decisive that the point cloud quasi represents a scenario of the monitoring area as a result of the depth camera device. The interpretation of this scenario may be carried out either in the depth camera device or in the monitoring system only. Two essential steps are to be distinguished in this connection. The first step is the basic creation of a scenario, for which the two middle steps of the method according to the present invention are used. Thus, an analysis of the point cloud is performed in a first step of this first part in order to achieve the detection of predefined objects. Predefined objects are different shapes and different contours or different volumes, which can be detected as such separately in the point cloud. Individual objects, e.g., tables, chairs or beds, as well as especially preferably persons can thus be detected. The detection is performed by the predefinition of these objects with corresponding object-specific parameters. This will be explained in more detail later.

The second step of this part of the method is used to carry out an exact determination of the location of the detected object in the monitoring area. This is the three-dimensional positioning in a first step independently from the time on the basis of a three-dimensional point cloud. Consequently, a scenario, in which information is available on detected predefined objects, on the one hand, and on the explicit locations of these objects in the monitoring area, on the other hand, will consequently develop as a result of these two steps of the part of the method. In the sense of the present invention, this first analysis of the information is also called scenario, which is available as a result of these two analysis and determination steps.

Subsequent to the creation of a scenario, different functionalities of this scenario can be developed. The analysis of the scenario may also be defined as an individual monitoring function of a method according to the present invention. What is common to all different functions of a method according to the present invention is the performance of a basic step. It is the comparison of the determined location of the at least one detected object with at least one predefined value for the location of this detected object. A number of parameters are involved here. Thus, a different predefined value can be defined for the particular desired location of this detected object for different objects. In other words, the predefined values are correspondingly likewise object-specific. The predefined value consequently contains a location position, at which this object shall be located as desired. A deviation of the actually detected or determined location of the detected object from the desired predefined value for this location thus also becomes detectable by the comparison. This distance can be used for monitoring for different functions. The simplest and clearest case is a function of the so-called "virtual fence," i.e., a virtual bed rail. An explicit location or a location quantity, at which the object may be located or may not be located, can thus be preset as a predefined value for the location of a detected object. The boundary between the locations that are defined as permissible and as non-permissible for the particular object may be called a virtual fence. Using a method according to the present invention, the scenario can consequently be analyzed so as to determine whether the object is located within or outside the virtual fence. If the object is a person recognized as a patient, this leads to the possibility of presetting a permission structure for this patient. If this patient is not allowed to leave his/her patient room and/or his/her bed for medical and safety reasons, such a virtual fence can guarantee this monitoring. If the patient as an object is located within this virtual fence, there is no reason for the method to generate an alarm for the hospital staff. If the object in the form of the patient is moving towards the virtual fence and even crosses it as a whole or with individual body parts, an alarm may be triggered, so that actions can correspondingly be taken immediately for bringing the patient back into his patient room. The above-described functionality is one of different possibilities for analyzing a scenario that is made available. It now becomes especially clear that greatly different functionalities may be based on the same scenario, so that data once made available from the point cloud and their analysis in the form of the scenario can be used several times for different monitoring functions. It also already becomes clear that the individual monitoring functions may be readily combined with one another for the reason without requiring additional effort for the data generation.

The above explanation of the individual steps is carried out repeatedly over time. Thus, both the step of creating the scenario in a four-dimensional manner and the steps of monitoring by the comparison are carried out. In other words, continuous performance of a method according to the present invention over time is thus achieved, so that quasi a four-dimensional monitoring is possible for the individual monitoring functions. Relative to the particular location of the object, a "tracking process" is performed, so to speak, following the detection of the object in a scenario, i.e., the object is tracked in respect to its location within the monitoring area.

A great variety of object-specific information may be taken into account in the step of analyzing the point cloud. For example, color information on the individual points of the point cloud may be used for this. Typical contours, which can be recognized from the point cloud, may point to corresponding objects, e.g., a table or a chair or a person. A detected expected volume may also be used qualitatively and/or quantitatively for the object-specific analysis of the point cloud. The actual location of the object, e.g., standing on the floor, may also be used as information for the analysis. Last but not least, the change in the respective corresponding points in the point cloud over time is also a source of information for the analysis in respect to predefined objects. In particular, static objects can be distinguished from moving objects especially quickly and simply in this manner.

It may be advantageous if the analysis of the point cloud or of a part of the point cloud for detecting at least one predefined object is performed in a method according to the present invention on the basis of predefined object-specific parameters, especially on the basis of at least one of the following parameters:

location of the point cloud,
change in the location of the point cloud over time,
contour of the point cloud,
change in the contour of the point cloud over time,
volume of the point cloud, and
change in the volume of the point cloud over time.

The above list is not a complete list. In particular, the change in the respective parameters over time should once again be pointed out, so that a motion profile of the particular object can thus also be used for the detection and the corresponding predefinition. The locations of the point cloud and the locations of the objects shall be defined in a three-dimensional manner as depth information. The contour is quasi a two-dimensional representation as a projection of the three-dimensional information of the depth camera device. A volume is an estimated volume on the basis of the information of the depth camera device, which information is, in turn, made again available three-dimensionally. Other information, e.g., from additional sensor devices of the depth camera device or of the monitoring system, may, of course, also be made available in order to carry out a corresponding analysis for detecting at least one predefined object. A combination of different object-specific parameters may, of course, also increase the accuracy with which predefined objects are detected and especially with which similar predefined objects are distinguished. The volume of the point cloud may also be limited by parts of objects, so that this volume is obtained as a space that is enclosed by the point cloud.

Another advantage can be achieved if an object detected as a person is detected in a method according to the present invention as a patient on the basis of at least one person-specific parameter, especially on the basis of at least one of the following person-specific parameters:

location of the person, explicit marking by a third person, e.g., by the environment input to be described later, and properties of the contour of the person.

In particular, the change over time in the respective parameter is taken into account as well. Thus, a person can still be detected relatively quickly and simply from a motion profile. However, the distinction between different persons and especially the definition of a person as a patient is of particular significance in monitoring, especially to avoid unnecessary false alarms. This definition is preferably performed in an initial training, so that a definition of a person as a patient, once performed, is maintained by the tracking of this patient. This is also true when the person defined as a patient may possibly be moving about within the monitoring area, a circumstance which does not fully satisfy the parameters specific of the patient any more. This may be called initialization of an object in the form of a person as a patient. For example, the fact that a person is getting into the bed in a monitoring area may be described now as an initial definition of this person as a patient. Other possibilities, e.g., the detection of the intubation of this person, is, of course, also conceivable for the definition as a patient. For example, a connection to adjacent medical devices, especially in the form of a ventilator (also known as a respirator), or the tracking of a flexible tube leading to the tube may be used to detect a tube. This will also be explained in more detail later.

Further, it may be advantageous if an alarm signal is generated in a method according to the present invention when a predefined deviation from the at least one predefined value for the location of the detected object is exceeded. An alarm signal is defined in the sense of the present invention as a deliberate and defined generation of information for a medical staff. Thus, a medical staff of a hospital may also be located in this case as well in a monitoring room in which this alarm is generated, e.g., in the form of an emergency nurse call. It is also possible to transmit this alarm directly to medical staff in the form of physicians to the pager or mobile telephone thereof. It thus becomes clear that the actual monitoring functionality is made available essentially even fully automatically. The actual medical intervention must be performed by medical staff only in case of a detected monitoring case, i.e., when an alarm is generated. The alarm signal may be divided into different alarm levels. It is thus possible, in reference to the described functionality of a virtual fence, to define different fences in a monitoring room, so that it will be possible to distinguish a pre-alarm from a master alarm. For example, a patient getting out of bed may trigger a pre-alarm, while leaving the room through the door will trigger the master alarm. This graduated alarming may also lead to different alarm paths, so that not only the medical staff but also a security service will be informed, e.g., when the patient leaves his room.

Different monitoring functions of a method according to the present invention will be explained in more detail below. What is involved here is essentially exclusively the second part of the method according to the present invention, i.e., the analysis of the particular scenario. It should already be noted that the same scenario is always made available by the use of a common scenario from the first two steps of the method according to the present invention, namely, the analysis of the point cloud and the determination of the location. This scenario is used by the different monitoring functions together, but with different results and different objectives. Furthermore, the monitoring functions described below differ by essentially one decisive point. Thus, it is of decisive significance for the subsequent analysis whether the predefined value has a reference point within another object or in an absolute manner in the monitoring area. A reference point in the monitoring area may also be defined as an absolute predefined value. A reference point at another object may be defined as a relative predefined value. It should be noted in this connection that an object may, of course, have individual partial objects. This is especially clearly apparent in case of an object in the form of a person, who may have individual objects due to partial objects due to limbs, articulation points or other body parts. Thus, individual objects may, of course, overlap or a large object may be composed of a plurality of small objects.

As was explained in the above paragraph, it may be advantageous if the at least one predefined value for the location of the detected object is formed in a method according to the present invention as an absolute predefined value relative to the monitoring area. This should mean that an absolute location definition is given as a predefined value for the location of the detected object relative to the monitoring area. There is no relation to other objects in this case or if there is, then only in addition to this absolute predefined value. An especially simple, cost-effective analysis and above all an analysis that is associated with a small amount of calculation effort becomes possible for a scenario that is created.

The so-called virtual fence is a possible monitoring functionality with an absolute predefined value in the sense of the present invention. This virtual fence may, of course, be freely combined with all other monitoring functionalities of the present invention. It may also unite in itself both absolute and relative predefined values in a combination.

It may consequently be advantageous if the at least one absolute predefined value in a method according to the present invention is a location boundary, which the detected object, especially a person defined as a patient, must not cross. This absolute predefined value may, of course, also be made available by a result of the analysis of the point cloud. As was already explained in the introduction, such a virtual fence is defined as a location boundary, which is defined, e.g., around a bed. If the person is moving beyond this location boundary, a corresponding alarm may be triggered. Different location boundaries may also be coupled here with different alarm levels, i.e., for example, with a pre-alarm and a master alarm. It is thus ensured that bedridden persons cannot leave their beds without skilled medical staff being alerted to it. Thus, there is quasi a security against the patient leaving his bed or the room in the monitoring area. It should be noted in this connection that this version of an absolute predefined value, designed as a location boundary, may, of course, also have a three-dimensional extension. Thus, a location boundary, which is crossed by the patient's upper body when he sits up in bed, may also be defined above the bed. Thus, sitting up in bed is already detected as exceeding an absolute predefined value, and a corresponding alarm signal may be generated. An additional location boundary in the area of the door of the patient room in the monitoring area may be defined for a master alarm in order to make it possible to trigger the master alarm when the patient is leaving the room.

A method according to the above paragraph may be perfected in such a way that in case of a first-time motion of the detected object in the form of a person beyond the location boundary, this person is defined as a patient. As was likewise explained above, it an advantage of the present invention that additional information can be assigned to individual objects in the form of persons. Thus, persons may be initially defined, e.g., as patients and they also continue to be defined as patients over the monitoring period due to the tracking of the locations of this person. For example, a location boundary may be placed around the bed in a patient room in the monitoring area. If a person crosses this location boundary and correspondingly gets into the bed in the patient room, it may be assumed with a high degree of probability that this person is a patient. Coupling with a minimum direction of crossing the location boundary may, of course, also be performed in order to also define the correct person as a patient with a higher level of safety. The fact that a bed with a person lying in it in a patient room may also be used to define the person located in it as a patient.

Another advantage is achieved if the steps of the method are performed in a method according to the present invention according to the above two paragraphs only for the section of the location of the monitoring area on the side of the location boundary on which the detected object is located. This is also an additional functionality of the "virtual fence" monitoring function. It becomes possible in this manner to reduce the section of the monitoring area that is actually being monitored, so that the necessary data sets and the corresponding analysis can correspondingly be reduced. If, for example, an inner area in the monitoring area is defined as the bed, the subsequent monitoring of the patient can be limited to the area within the location boundary around the bed in case of a patient who has laid down in the bed. The reduction of the data set may relate here to the generation of the point cloud, on the one hand, and to the analysis of said point cloud to create the scenario, on the other hand.

Moreover, a further monitoring functionality is possible in case of a design of the method according to the present invention. Thus, sedation monitoring can be performed, which monitors the sedation and hence the immobilization of a patient. This also preferably involves the use of absolute predefined values in the sense of the present invention.

It may thus already be advantageous if the at least one absolute predefined value in a method according to the present invention is a maximum and/or minimum change in the location of the detected object over time. In other words, even the gradient of the change over time is preferably monitored, so that an activity index can be generated, which is correlated with the actual activity of the patient. The patient in question may be monitored as a whole or individual limbs of the patient may be monitored as partial objects of the person. The activity index is consequently used to detect the actual activity of individual body parts and thus to infer the current activity situation of the patient. It thus becomes possible that the current activity is related to the desired sedation. If a patient is provided with intense sedation, a lower activity is also correspondingly presumed. If, however, a higher activity, i.e., a greater change in the locations of the object over time can, on the contrary, be detected compared to a preset activity, the dosage of the sedation must be assumed to be very likely to be too low. A corresponding alarm may likewise be generated in this case.

For example, individual points of the skeleton of a person can be detected as partial objects of this person in the point cloud. The activity index becomes even more accurate and detailed in this manner and it becomes possible to detect the quality of sedation even more accurately and in more detail. A so-called delirium monitoring functionality may, of course, also be made available based on the activity index in the opposite way. It also becomes possible to detect a person, who becomes too calm in an undesired manner, i.e., for example, becomes comatose. It becomes clearly visible here that the monitoring functionality of the sedation monitoring and the monitoring functionality of delirium monitoring are preferably used combined with one another. Any desired number of limits can be set here to make available an alarm in the particular direction, i.e., for example, in the direction of sufficient sedation and delirium monitoring.

It may, furthermore, be advantageous in sedation monitoring according to the above paragraph if the predefined and detected object is at least one body part of a person in the method according to the present invention. It can be assumed here, in particular, that the extremities of the person in the form of fingers, hands, arms or legs represent the best predictive value concerning the current activity index. The eyelids of the person may also be monitored, e.g., in case of a corresponding resolution of the depth camera device. It thus becomes possible to achieve an even further improvement of a sedation monitoring as a monitoring functionality of a method according to the present invention.

It may, moreover, be advantageous in sedation monitoring as a functionality of a method according to the present invention if the absolute predefined value can be set in the form of the maximum and/or minimum change in the location of the detected object. Thus, sedation of a patient may take place in different quantities. For example, a person can be completely immobilized, so that it can be assumed that there is essentially no activity whatsoever. An only mild sedation may also ensure calming of a patient, who otherwise has an only slightly slowed-down activity. To improve the monitoring and to avoid false alarms, the activity index or even directly the respective predefined values may be set for the corresponding maximum or minimum change of the location of the detected object.

The monitoring functionality may be set by hand or by so-called environment input. Environment input is defined in the sense of the present invention as an active switching on of the respective monitoring functionality by the method according to the present invention itself. If, for example, a ventilator is detected in the monitoring area, a corresponding monitoring of ventilation is performed. If, for example, a sedating device is detected as an object by a method according to the present invention, the above-described monitoring functionality of sedation monitoring may be performed. The environment input may also be brought about, e.g., by the inclination of the bed or the position of a bed rail.

Further, it is advantageous in a monitoring functionality in the form of a sedation monitoring if the change in the location of the detected object over time takes place by means of the mean square error of the determined location of the detected object in the method according to the present invention. The monitoring is quasi averaged in this case to reduce the fault liability. This mean square error pertains, in particular, to the particular locations of positions of the skeleton or positions of the limbs of the person.

To make available an additional monitoring in the method according to the present invention, it is possible to carry out, for example, a monitoring for seizures. A combination with all other monitoring functionalities of the present invention may likewise be made for this on the basis of a common scenario from the point cloud.

Thus, it may be advantageous if the at least one absolute predefined value in a method according to the present invention is the rhythm of the change in the location of the detected object over time. In case of a seizure, the latter will lead in most cases to twitching of the limbs of the person. The monitoring is therefore performed with respect to the corresponding limbs of the person, which represent individual objects each. It appears that even the absolute monitoring with respect to the actual and absolute location of the limb in question in space and the monitoring thereof over time make it possible to detect a rhythm in the motion of this object in the form of a limb. However, a relative viewing may, of course, also additionally take place, so that relative motions of individual limbs in relation to one another are likewise monitored for rhythmic twitching. In particular, a person as a whole may also be monitored, in addition to the monitoring of partial objects, so that a grid, which performs a pulsating change in case of motion of the person, is quasi created for this person by the point cloud. If this pulsation of the point cloud for the object in the form of the person or patient takes place rhythmically (and/or cadent and/or with a periodic nature), the corresponding alarm of monitoring for seizures can be generated. The rhythm for the change in the location of the detected object over time can be described as being rapid and recurrent. It becomes clear here as well that additional sensors can yield additional information for the monitoring functionality in the form of the monitoring for seizures. This information may be, e.g., color information, which can make it possible to detect the blue color of the lips or the color of the face.

It may be advantageous in the monitoring functionality of monitoring for seizures if the following steps are carried out in a method according to the present invention:
 a detection or determination of at least two predefined objects in the form of adjacent joints of a limb of a person,
 a determination of the vector between a proximal joint and a distal joint, and
 an insertion of the determined vector into a time series.

The above steps represent a preferred embodiment for generating a monitoring functionality in the form of a monitoring for seizures. Not only one limb, but preferably a plurality of limbs of the person are monitored. The joint in question may be defined as a joint point in the point cloud. The particular limbs may be selected on the basis of the susceptibility to seizures. Monitoring or definition of the type of the seizure may also be performed during the monitoring of a plurality of limbs on the basis of the limb that develops a seizure or is performing rhythmic motions. When objects are detected, especially their contour is taken into account, so that coverage by clothing or a blanket plays no decisive role for the functionality of the method according to the present invention.

It may, further, be advantageous in the monitoring functionality of monitoring for seizures according to the above paragraph if at least two limbs are monitored in a method according to the present invention, and a comparison of a rhythmic change of the particular location is compared with a predefined minimum duration. It is thus ensured in case of a seizure situation that what is involved is actually a seizure rather than short-term twitching of the corresponding limb. The minimum duration correspondingly preferably prevents a false alarm in case of short-term twitching of the limb in question of the person. A typical motion pattern is also taken into account here, so that changes in the particular twitching rhythm can reflect a course of the seizure over time.

Another monitoring functionality according to the present invention may be carried out during the analysis of the scenario in monitoring for falling. It can be ensured that falling of the person in question and, associated therewith, a corresponding injury are recognized in time and emergency assistance can correspondingly be offered. The safety of the person within the monitoring area can be further increased.

It is advantageous for generating a monitoring functionality in the form of monitoring for falling if the at least one absolute predefined value in a method according to the present invention is the distance of the determined location of the at least one detected object, especially in the form of the head of a person, from the floor and/or a wall of the monitoring area. If the head is detected as the object of the person, the distance of the head not only from the floor but also from the wall can provide information on whether this person is in the upright or recumbent position. Especially rapid changes and reductions of the distance from the floor and/or from the wall are very likely to indicate falling of the person. Due to the correlation with wall sections of the monitoring area, an oblique falling against the wall is thus detected as falling and safety is correspondingly increased further during the monitoring functionality of a monitoring for falling.

A functionality in the form of a nurse call is likewise a possible monitoring functionality in a method according to the present invention. This is defined as the detection of gestures that contain an alarm in the form of a call for help for additional staff of the medical institution or hospital.

It may be advantageous in a monitoring functionality for a nurse call if the at least one absolute predefined value in a method according to the present invention is the change in the determined location of the at least one detected object, especially in the form of a limb of a person, compared to a predefined change of the location of the at least one detected object. In other words, it becomes possible to define gestures and to preset them as a change in the location of the object in question, which gestures can trigger an alarm for a nurse call in the manner according to the present invention. For example, a motion of the arm, a motion of the head or a motion of a hand may trigger the corresponding alarm for a nurse call. It should be noted in this connection that this leads to great advantages not only for the patient but also for the staff within the monitoring area. If, for example, a sterile procedure is required, no non-sterile button needs to be pushed any more for the nurse call, but the desired alarm can be triggered by a gesture by a sterile procedure.

As was already explained above, not only absolute predefined values, but also relative predefined values may be used for carrying out a method according to the present invention. A relative predefined value is the location of the detected object with reference to the location of another detected object. Monitoring functionalities with relative predefined values may, of course, also be combined with monitoring functionalities with absolute predefined values. Relative predefined values and absolute predefined values may also be used together within a monitoring function.

Thus, it may be advantageous if the at least one predefined value for the location of the detected object is a relative predefined value relative to the monitoring area in a method according to the present invention. In other words, the method is carried out for at least two predefined and detected objects, so that the relative arrangement of these objects in relation to one another is used as an input value for a corresponding monitoring functionality. This relative functionality may be freely combined with other monitoring functionalities.

A so-called tube monitoring is an especially advantageous solution for a monitoring functionality with relative predefined values. This is used to prevent persons from removing medical devices or accesses from their bodies. These are especially intubation components, such as ventilation tubes, catheters and drains for introducing and draining liquids, compresses for hemostasis management as well as masks for ventilation or for eye protection, which are introduced into or are in close contact with the patient's body. Removal of such medical components would be associated with a great risk, so that this monitoring functionality of tube monitoring correspondingly leads to a great increase in safety.

To make tube monitoring available, it may be advantageous if the at least one relative predefined value in a method according to the present invention is the distance of the locations of a first detected object and at least one second detected object of a person. It becomes clear here that the person as an object may have individual partial objects, likewise as objects of his own. For example, the area of the neck, in which a ventilation tube is arranged, may be defined as a second object. The tube itself may also be able to be defined as a second object due to its connection to the person or to the patient. The first object may be, e.g., the hand of the patient, so that a motion of the hand to the tube can be recognized as a risk. If the hand reaches the tube as an object, there is a risk of the patient grasping and pulling it out. The master alarm may now be triggered, as it was already explained several times.

It may, furthermore, be advantageous in a monitoring functionality in the form of tube monitoring if the first detected object in a method according to the present invention is a limb of the person, especially a hand or a finger, and the second object is a tube placed on the person. The limb may, of course, also comprise a plurality of limbs, so that all fingers and the ball of the hand together define the hand as a limb. It becomes possible in this manner, in particular, to predefine a minimum distance, which already defines the touching of the tube in question as an alarm situation in monitoring. The method can correspondingly be carried out for the tube in a specifically predefined manner. The detection of the individual objects as a tube or as a limb can be checked preferably continuously in order to avoid monitoring errors.

It is advantageous, moreover, if the second object in the form of a tube is detected due to its dependence on at least one additional object in a monitoring functionality in the form of a tube monitoring in a method according to the present invention. For example, a ventilator may be arranged in the monitoring area in case of an intubated patient. A syringe pump may be detected in the monitoring area in case of a patient with a venous or arterial access. To ensure ventilation via the tube, a ventilation tube is usually provided, which is connected to the tube. As additional information, this information can make it possible to locate the tube. When a ventilator is detected, the monitoring functionality of tube monitoring is quasi activated, in principle, as an environment input for a method according to the present invention. The activity of a device, i.e., whether it is switched on or switched off, may also take place by an environment input and hence by detection by means of the method according to the present invention. The presence of another person, especially medical staff, may also be used as an environment input. The tube can subsequently be defined by the object detection of the ventilation tube and the three-dimensional tracking thereof at its opposite ends. The intersection between the ventilation tube and the object in the form of the patient is consequently the location of the tube. An object can thus be explicitly defined by correlation with additional objects, even if it should be too small in the form of the tube for a corresponding resolution of the depth camera device. Increased safety is thus combined with reduced detection qualities of the depth camera device.

It may, further, be advantageous in a monitoring functionality in the form of tube monitoring if a surrounding first enveloping body is formed for the first object and a surrounding second enveloping body is formed for the second object in a method according to the present invention, and a collision of the two enveloping bodies is monitored. An enveloping body is a body around the object in question. The object is preferably defined here in a punctiform manner, as this will be explained later. The enveloping body may have, in principle, a free geometric shape. However, an essentially spherical shape is preferred, so that the enveloping body becomes able to be defined simply and rapidly by specifying a predefined radius as the only parameter. An alternative enveloping body may also have another geometry, e.g., in the form of an enveloping box. The length, width and angle of rotation are specified here as parameters. The collision of the two enveloping bodies is consequently an intersection of the two enveloping bodies, which can be defined as the crossing over of a predefined boundary. A time alarm thus becomes possible depending on the size of the particular enveloping body, so that an alarm is triggered already before the patient's hand and the tube come into contact with one another.

A further advantage is achieved in the monitoring functionality in the form of a tube monitoring if at least two second objects are detected in a method according to the present invention, and a combined enveloping body is formed for the individual enveloping bodies of the second objects. It is, of course, also possible to form a plurality of objects as second objects. For example, the tube can be detected as a second object in case of a tube inserted in the throat. The patient's head and also the patient's sternum may represent an additional second object, so that, on the whole, three enveloping bodies are predefined for three second objects. These three enveloping bodies can be correlated to a common enveloping body, so that a complex enveloping body becomes possible through the simple addition of individual objects from the point cloud for a correspondingly increased accuracy of detection in the monitoring system and in the monitoring method.

It may, furthermore, be advantageous in tube monitoring as a monitoring functionality if the particular enveloping body is formed around a center of gravity of the object in question in a method according to the present invention. The center of gravity is a punctiform extension of the object in question and can be defined as the starting point for the enveloping body. It thus becomes possible to define an individual and punctiform extension of the object and to adapt the real extension of the object by the corresponding size and shape of the enveloping body. The definition of the center of gravity as a point is performed in the assessment of the scenario and in the creation of the scenario in the point cloud.

Moreover, the distance of the locations can be taken into account in relation to time, especially in relation to a minimum duration during which an actual distance is shorter than a predefined minimum distance in a monitoring functionality in the form of a tube monitoring in a method according to the present invention. A collision of individual enveloping bodies, as it was already explained, can thus be allowed for a short time before the alarm is triggered only after a minimum duration. The probability of false alarms can also be markedly reduced in this way depending on the patient's situation.

Further possible steps of a method according to the present invention, which can be combined with both absolute predefined values and relative predefined values, will also be explained below.

It is thus possible that at least one preliminary stage predefined value is predefined and used for the comparison in addition to the at least one predefined value in a method according to the present invention. This is a so-called preliminary stage for generating a pre-alarm as opposed to a master alarm. It is, of course, also possible to use a plurality of preliminary stage predefined values in order to achieve corresponding safety graduations in alarm generation. In particular, different medical staff members can be notified, depending on the degree of the alarm generated during the monitoring. Thus, it may be sufficient, for example, that security staff is informed, or a member of the medical staff must be called even directly in an extreme case.

Another advantage can be achieved if the step of comparison of a functionality of the method is activated in a method according to the present invention. This is defined as the environment input already mentioned several times before. Modes of action can thus be defined for the method from the monitoring of individual detected objects in respect to their location. For example, it may be advantageous to monitor the bed in terms of its structure when designing a monitoring functionality in the form of a virtual fence. If a person, who is defined as a patient, is located within the bed, it is decisive for switching on the monitoring functionality in the form of the virtual fence that, e.g., the bed rail is raised. Other environment inputs are also possible in the sense of the present invention to switch on individual monitoring functionalities.

Another advantage can be achieved if an object detected as a person is monitored over the course of time with respect to his location in a method according to the present invention. In other words, a so-called tracking of this person is performed. In particular, this is performed for the particular person in order to make it possible to trace a corresponding motion profile for the digital patient file. Even if an alarm fails, the path leading to the alarm situation can be traced in this way. Adaptation of the monitoring parameters of the individual monitoring functionalities is also conceivable on the basis of the motion profile of the patient in the monitoring area.

Another advantage may be if a step of storing the determined locations or location classes (close to the head, in the bed, at the ventilator) of the at least one detected object is carried out in a method according to the present invention. This storage is carried out especially combined with the embodiment according to the above paragraph, so that a digital patient file with the patient's case history is made available for a patient as a person. This also pertains, of course, in particular, to the alarm events during the monitoring phase. A correlation with other alarm events of additional devices, which are especially related directly to the patient, is also advantageous. For example, the information on the motion of the patient can be used to determine certain signal artifacts as such. It becomes clearly apparent here how broadly a method according to the present invention is used. For example, use in a patient lock before a surgery, in which the patients usually wait in their bed alone, is thus also possible.

The present invention also pertains to a monitoring system, having a depth camera device for monitoring a monitoring area and a control unit. The monitoring system according to the present invention is characterized in that the control unit is designed for carrying out a method according to the present invention. A monitoring system according to the present invention correspondingly offers the same advantages as those explained in detail with reference to a method according to the present invention.

Further advantages, features and details of the present invention appear from the following description, in which exemplary embodiments of the present invention are described in detail with reference to the drawings. The features mentioned in the claims and in the specification may be essential for the present invention each individually or in any desired combination.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
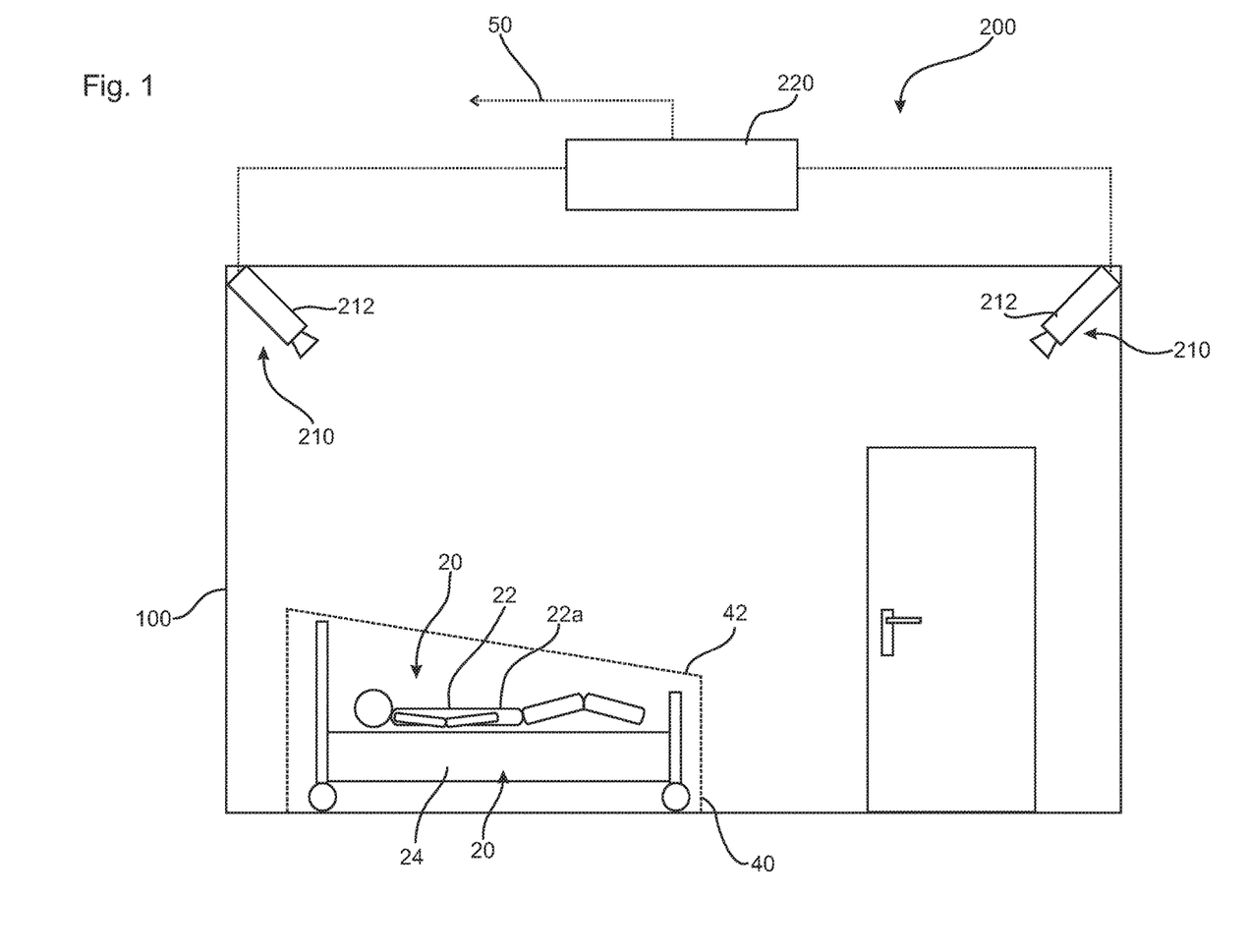
FIG. 1 is a schematic view of a monitoring area.
Figure 2:
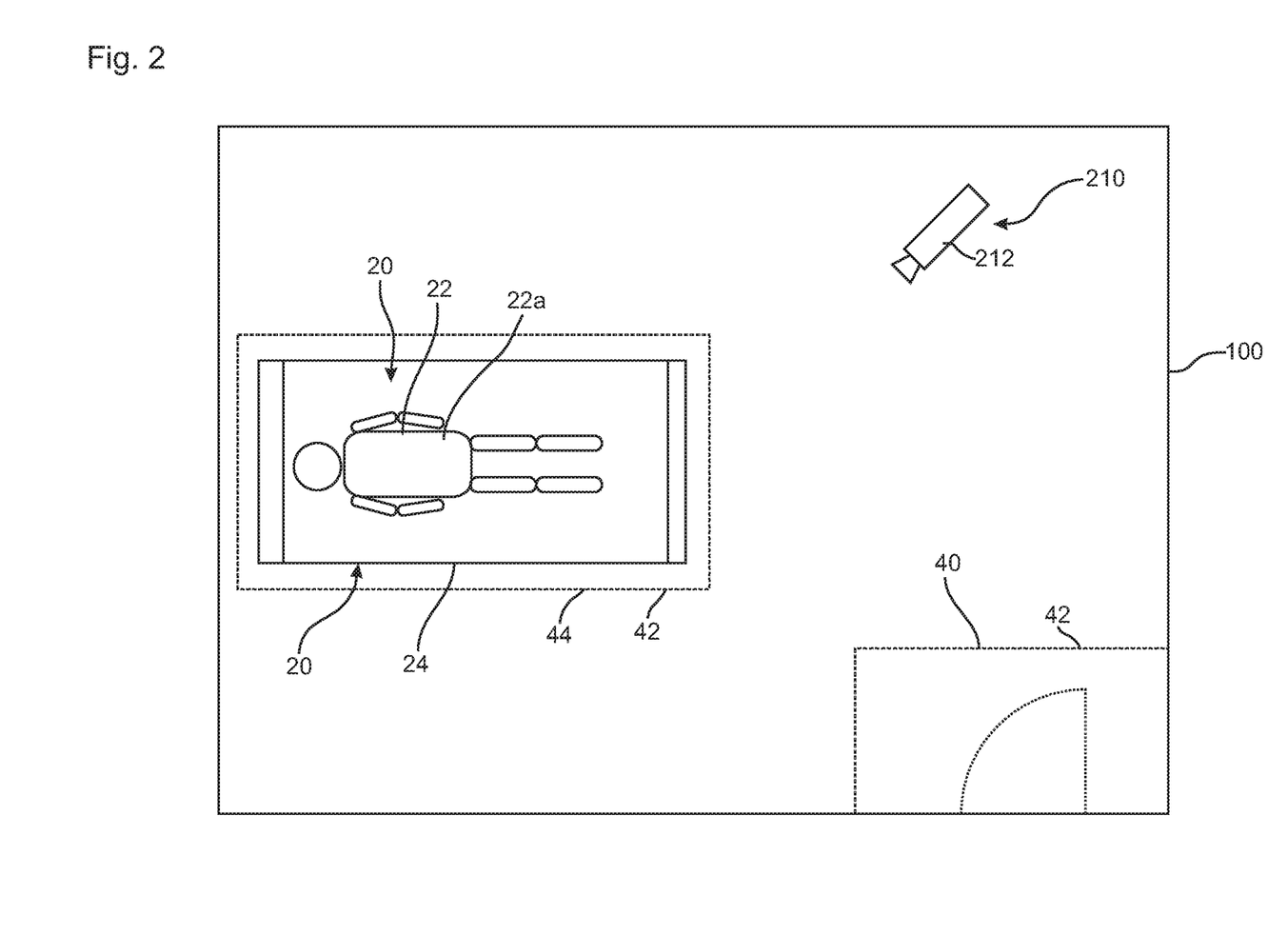
FIG. 2 is the embodiment according to FIG. 1 in a top view.

FIGS. 1 and 2 schematically show a monitoring area 100 in the form of a patient room. A monitoring system 200 with a control unit 220 for carrying out a method according to the present invention can be clearly seen. The monitoring system 200 is equipped, further, with a depth camera device 210 with two depth cameras 212 each. Depending on the monitoring functionalities switched on, a great variety of alarms 50 can be triggered by the control unit 220, The alarm may be transmitted, e.g., to an emergency call system of a pager of a physician or into a monitoring room of a hospital. Storage for documentation purposes or for transmission to an IT system of the hospital is also conceivable.

As can be clearly seen in FIG. 1, an object 20 in the form of a bed 24 is arranged within the monitoring area 100. An object 20 in the form of a person 22 is located within the bed 24. This person 22 has gotten into the bed or was laid into the bed or was moved with the bed into the room and has crossed a location boundary 42. By crossing when getting into the bed 24, the person 22 could be defined as a patient 22a. A person 22, who was initialized and defined as a patient 22a, is consequently located in the object 20 in the form of the bed 24 for the status according to FIG. 1. This can be called the safe state.

FIG. 2 shows in a top view that the location boundary 42 can be predefined at two points. In particular, it is a three-dimensionally extending location boundary 42 in both cases.

The location boundary 42 at the two different positions thus forms a predefined value 40 and a preliminary stage predefined value 44. If the patient 22a is moving about of the bed 24, the patient will first cross the location boundary 42 of the preliminary stage predefined value 44. A pre-alarm can be triggered hereby as an alarm signal 50 by the control unit 220. If the patient 22a is moving towards the door, the patient will cross, at a determined time, the additional location boundary 42 in the form of the predefined value 40, so that the control unit 220 will in this case send the master alarm as an alarm signal 50. The functionality being described here is a monitoring function in the form of a virtual fence.

Figure 3:
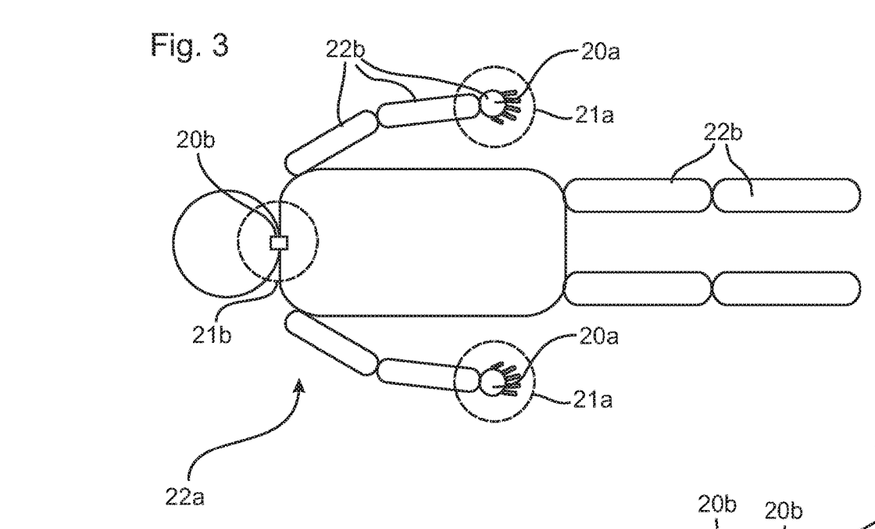
FIG. 3 is a schematic view of a patient in a top view.

In a top view, FIG. 3 schematically likewise shows a person 22 defined as a patient 22a as an object 20. This object has a plurality of limbs 22b. These are especially the legs, arms and hands. A monitoring functionality is embodied in this embodiment in the form of a tube monitoring. The objects decisive for this are, according to FIG. 3, the two hands as limbs 22b. Another decisive object 20 is a second detected object 20b in the form of a tube at the neck of the patient 22a. An enveloping body 21a and 21b each is defined in a spherical manner around both detected objects 20a and 20b. The distance between these respective enveloping bodies 21a and 21a now defines a distinction between a safe situation and unsafe situation for the patient 22a.

Figure 4:
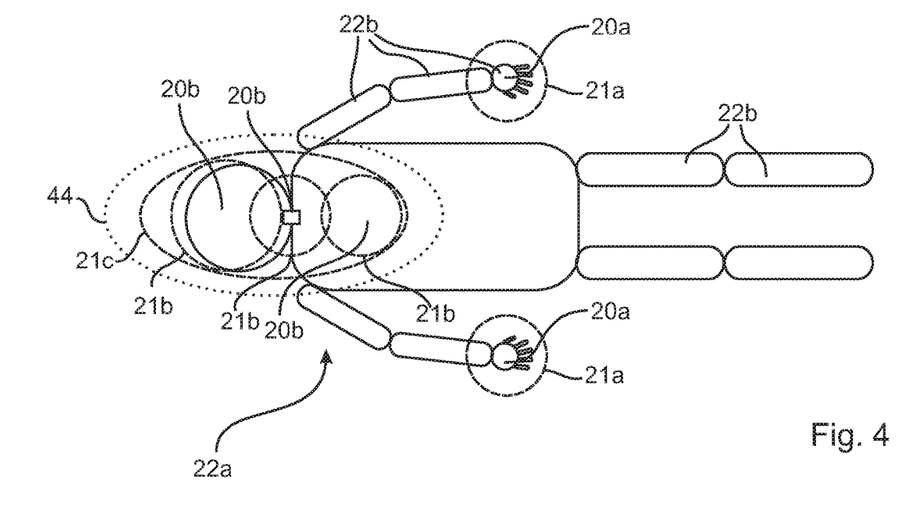
FIG. 4 is another schematic view of a patient in a top view.
Figure 5:
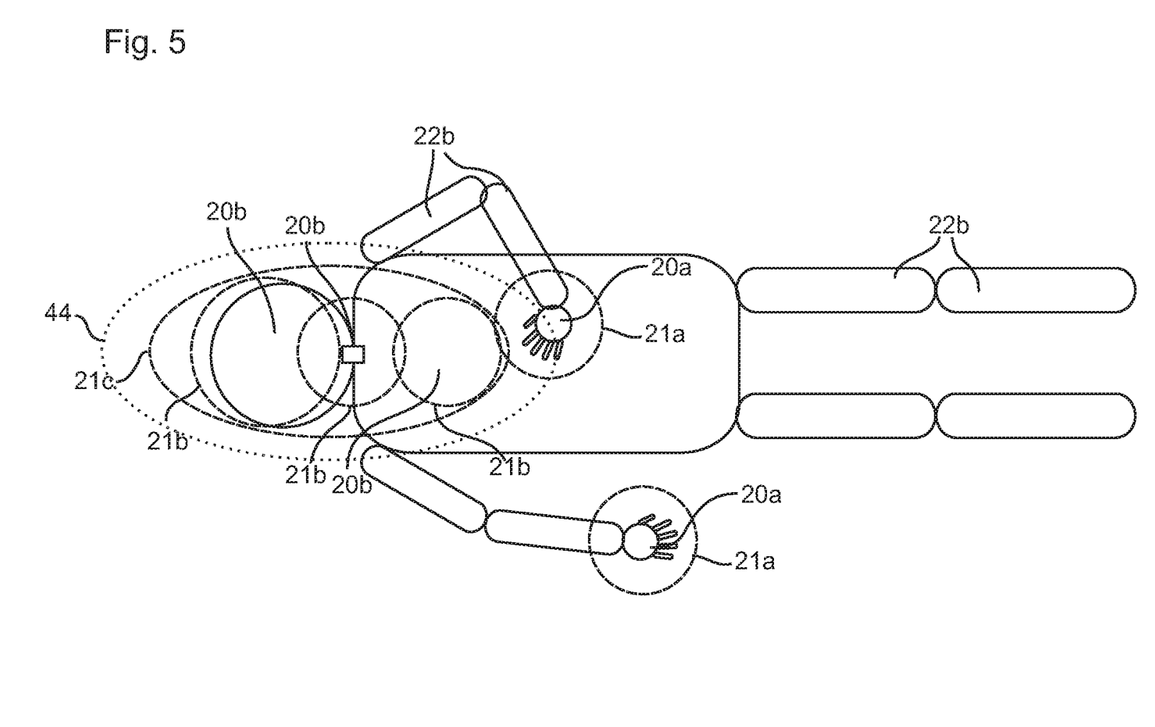
FIG. 5 is the view according to FIG. 4 with a situation in which a limb is moving.

FIGS. 4 and 5 show a more complex solution for the monitoring functionality of tube monitoring. Thus, a plurality of objects 20 to be monitored are indicated here. On the one hand, these are again the two hands of the patient 22a with corresponding first enveloping bodies 21a as the first detected objects. Further. the head of the patient 22a, the sternum of the patient 22a and the above-described tube are second detected objects 20b correspondingly with three corresponding second enveloping bodies 21b. These can be combined into a combined enveloping body 21c, which is now monitored against collision with the first enveloping bodies 21a.

FIG. 4 also shows a solution which provides the monitoring functionality of tube monitoring with a preliminary stage predefined value 44. It is a further enlarged combined enveloping body 21c, which is defined as a preliminary stage predefined value 44 in this case.

FIG. 5 shows a situation which triggers the master alarm as an alarm signal 50. The left hand of the patient 22a has moved here in the direction of the tube to the extent that the preliminary stage predefined value 44 has already been exceeded. The first enveloping body 21a also penetrates the combined enveloping body 21c, so that the master alarm has also been triggered as an alarm signal 50.

Figure 6:
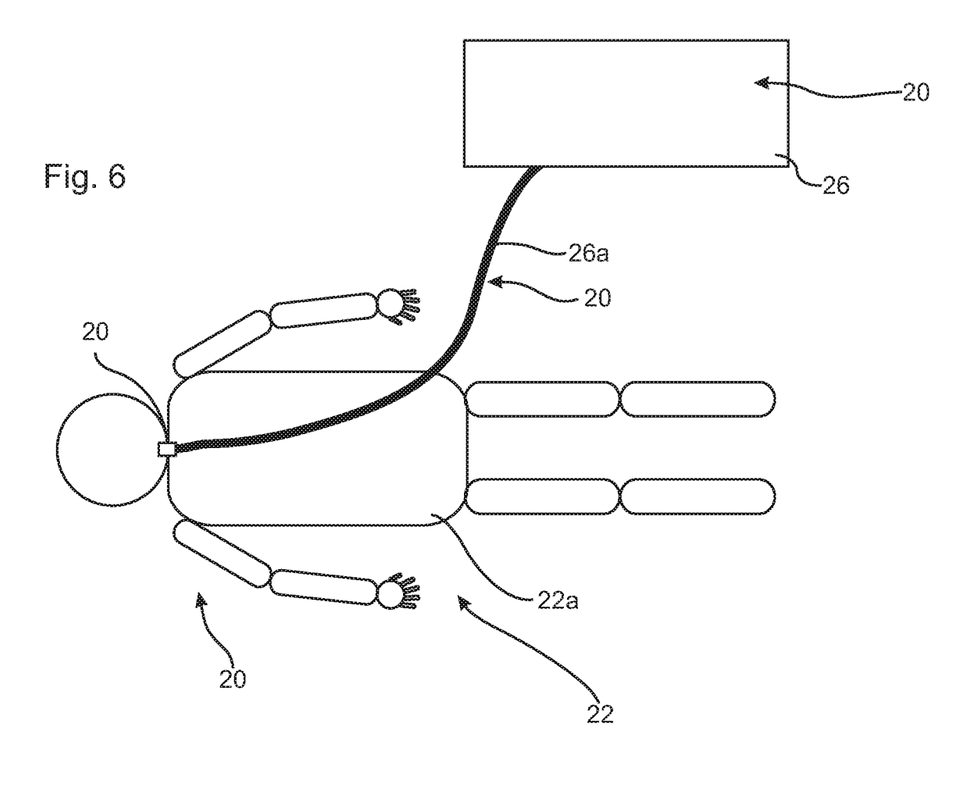
FIG. 6 is a schematic view of an intubated patient.

It is schematically shown in FIG. 6 how a detection of the position of the tube can be carried out. If, for example, the resolution of the depth camera 212 in question is not sufficient to directly detect the tube, a tube tracking may be made available for this. A ventilator 26 can thus be detected as an object 20. A ventilation tube 26a as an object 20 leads from this ventilator 26 to the patient 22a. The intersection between the ventilation tube 26a and the patient 22a is the point at which the tube must be placed. The tube thus becomes detectable as a separate object 20 based on the correlation with additional objects 20.

The possibility of a described environment input can also be explained by FIG. 6. Thus, it is recognized by the detection of a ventilator 26 and a connected ventilation tube 26a, namely a ventilation tube connected to the patient 22a, that the situation is a ventilation situation. The monitoring functionality of tube monitoring can now be switched on on the basis of this information.

The views shown in FIGS. 3 through 5 can also be used in a similar manner, with or without enveloping body, for generating further monitoring functionalities. Thus, the individual limbs 22b of the person 22 can also be used for generating an activity index for sedation monitoring. Delirium monitoring can also be performed in this way. In addition, the monitoring functionality of monitoring for seizures can be made available by monitoring rhythmic motions of individual limbs 22b. As was already explained several times, it also becomes clear that a great variety of monitoring functionalities can be achieved on the basis of an individual scenario by placing different aspects in the focus of the analysis.

Figure 7:
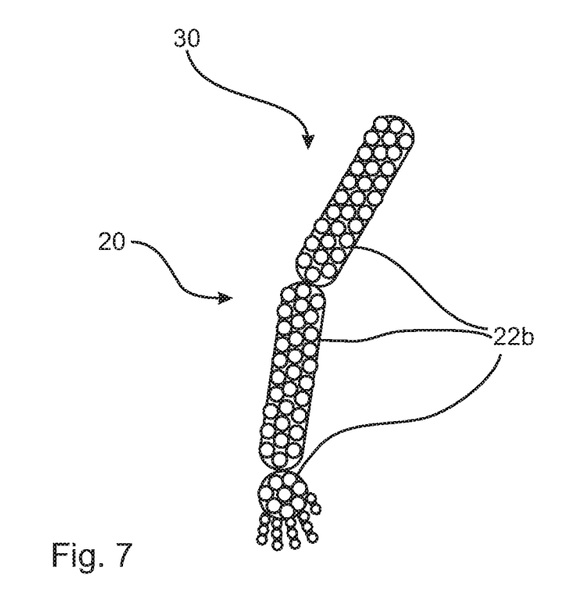
FIG. 7 is a schematic view of a point cloud.

FIG. 7 schematically shows a point cloud 30, which was recorded by the depth camera device 210 and was made available. The correlation can already be recognized here in the analysis, i.e., when a scenario is generated. Limbs 22b of the object 20 were formed here from the point cloud 30.

The above explanation of the embodiments describes the present invention exclusively within the framework of examples. Individual features of the present invention may, of course, be freely combined with one another if technically meaningful, without going beyond the scope of the present invention.

While specific embodiments of the invention have been shown and described in detail to illustrate the application of the principles of the invention, it will be understood that the invention may be embodied otherwise without departing from such principles.

The invention claimed is:

1. A method for monitoring a patient within a medical monitoring area the method comprising the steps of:
    providing a monitoring system with a depth camera device;
    generating a point cloud of the monitoring area with the monitoring system;
    analyzing the point cloud for detecting predefined objects;
    determining a location of at least one detected object in the monitoring area;
    comparing the determined location of the at least one detected object with at least one predefined value for the location of the at least one detected object;
    wherein the above steps are repeatedly performed over time so that a four-dimensional monitoring and thus with respect to the respective location of the object a tracking process is performed;
    determining if the at least one detected object is a person during the performance of the above steps, and if so creating a motion profile of the person from the locations of the person for a digital patient file;
    storing the locations of the at least one detected object in the digital patient file,
    the at least one predefined value for the location of the at least one detected object is formed as an absolute predefined value relative to the monitoring area.

2. A method in accordance with claim 1, wherein an object detected as a person is detected as a patient on the basis of at least one person-specific parameter, comprising at least one person-specific parameter from a set of person-specific parameters comprising:
    location of the person; and
    properties of the contour of the person.

3. A method in accordance with claim 1, wherein an alarm signal is generated when a predefined deviation from the at least one predefined value for the location of the detected object is exceeded.

4. A method in accordance with claim 3, wherein:
the path of the person provided by the motion profile leads to an alarm situation that generated the alarm signal.

5. A method in accordance with claim 1, wherein the at least one absolute predefined value is a location boundary, which the detected object, as a person defined as a patient, must not cross.

6. A method in accordance with claim 5, wherein the person is defined as a patient during a first-time motion of the detected object in the form of a person across the location boundary.

7. A method in accordance with claim 5, wherein the steps of the method are carried out only for a section of the location of the monitoring area on a side of the location boundary, on which side the detected object is located.

8. A method in accordance with claim 1, wherein the at least one absolute predefined value is a maximum change of a location of the detected object over time or a minimum change of the location of the detected object over time or both a maximum change of a location of the detected object over time and a minimum change of the location of the detected object over time.

9. A method in accordance with claim 8, wherein the predefined and detected object is at least one limb of a person.

10. A method in accordance with claim 1, wherein the absolute predefined value is formed as a value that can be set in the form of a maximum change of a location of the detected object or a minimum change of the location of the detected object or both a maximum change of a location of the detected object and a minimum change of the location of the detected object.

11. A method in accordance with claim 10, wherein the change of the location of the detected object over time takes place by means of the root mean square error of the determined location of the detected object.

12. A method in accordance with claim 1, wherein the at least one absolute predefined value is a rhythm of the change of the location of the detected object over time.

13. A method in accordance with claim 12, further comprising the steps of:
detecting at least two predefined objects in the form of adjacent joints of a limb of a person;
determining a vector between a proximal joint and a distal joint; and
inserting the determined vector into a time series.

14. A method in accordance with claim 13, wherein at least two limbs are monitored, and a comparison of a rhythmic change of a respective location is compared to a predefined minimum duration.

15. A method in accordance with claim 1, wherein the at least one absolute predefined value is a distance of the determined location of the at least one detected object, in the form of the head of a person, from a floor of the monitoring area or from a wall of the monitoring area or from both a floor of the monitoring area and from a wall of the monitoring area.

16. A method in accordance with claim 1, wherein the at least one absolute predefined value is the change of the determined location of the at least one detected object, compared to a predefined change of the location of the at least one detected object.

17. A method in accordance with claim 1, wherein the at least one predefined value for the location of the detected object is formed as a relative predefined value relative to the monitoring area.

18. A method in accordance with claim 17, wherein the at least one relative predefined value is a distance of the locations of a first detected object and at least one second detected object of a person.

19. A method in accordance with claim 18, wherein the first detected object is a limb of the person and the second detected object is a tube placed on the person.

20. A method in accordance with claim 19, wherein the second object in the form of a tube is detected by a dependence of the second object in the form of a tube on at least one additional object.

21. A method in accordance with claim 18, wherein a surrounding first enveloping body is formed for the first object and a surrounding second enveloping body is formed for the second object, and a collision of the two enveloping bodies is monitored.

22. A method in accordance with claim 21, wherein at least two second objects are detected, and a combined enveloping body is formed for the individual enveloping bodies of the second objects.

23. A method in accordance with claim 21, wherein the first enveloping body is formed around a center of gravity of the first object;
the second enveloping body is formed around a center of gravity of the second object.

24. A method in accordance with claim 18, wherein the distance of the locations is taken into account in relation to a minimum duration for an actual distance dropping below a predefined minimum distance.

25. A method in accordance with claim 1, wherein at least one preliminary stage predefined value is predefined and used for the comparison in addition to the at least one predefined value.

26. A method in accordance with claim 1, wherein the step of comparison activates at least one functionality of the method.

27. A method in accordance with claim 1, wherein an object recognized as a person is monitored over the course of time in respect to a location of the person.

28. A method in accordance with claim 1, further comprising a step of storing the determined locations of the at least one detected object.

29. A method in accordance with claim 1, wherein:
the motion profile provides a path of the person that can be traced.

30. A method for monitoring a patient within a medical monitoring area, the method comprising the steps of:
providing a monitoring system with a depth camera device;
generating a point cloud of the monitoring area with the monitoring system;
analyzing the point cloud for detecting predefined objects;
determining a location of at least one detected object in the monitoring area;
comparing the determined location of the at least one detected object with at least one predefined value for the location of the at least one detected object;
wherein the above steps are repeatedly performed over time so that a four-dimensional monitoring and thus with respect to a respective location of the object, a tracking process is performed to create a motion profile that provides a path of the object that can be traced over said repeatedly performed steps;

wherein the at least one predefined value for the location of the detected object is formed as an absolute predefined value relative to the monitoring area.

31. A method in accordance with claim 30, wherein:
the at least one absolute predefined value is a location boundary which a patient must not cross;
the steps of the method are carried out only for a section of the monitoring area on a side of the location boundary, on which side the at least one detected object is located.

32. A method in accordance with claim 30, wherein:
the at least one absolute predefined value is a rhythm of the change of the location of the detected object over time.

33. A method for monitoring a patient within a medical monitoring area, the method comprising the steps of:
providing a depth camera device;
generating a plurality of three dimensional point clouds of the monitoring area with the depth camera device over time;
analyzing the point clouds to detect a plurality of objects in the point clouds;
determining locations over time of the objects with respect to the monitoring area;
providing a plurality of monitoring functionalities for the plurality of objects, each of the plurality of monitoring functionalities including comparing locations of one of the plurality of objects with a predefined value for the location of the one object;
selectively performing one of the plurality of monitoring functionalities.

34. A method in accordance with claim 33, wherein one of the plurality of monitoring functionalities includes:
determining first relationships between the locations of the one object and a first predetermined location;
generating a first alarm to a caregiver when one of the first relationships is in a first range;
determining second relationships between the locations of the one object and a second predetermined location;
generating a second alarm to the caregiver when one of the second relationships is in a second range, one of the second predetermined location and the second range being different than the respective first location and first range, said second alarm being more severe than said first alarm.

35. A method in accordance with claim 33, wherein one of the plurality of monitoring functionalities includes:
identifying the one object as a function of changes in locations of the one object.

36. A method in accordance with claim 35, wherein
said identifying of the one object is performed as a function of the locations of the one object relative to a location of another object of the plurality of objects.

37. A method in accordance with claim 33, wherein one of the plurality of monitoring functionalities includes:
determining, in one of said plurality of point clouds, a location of a predetermined area in the monitoring area, the predetermined area being less than the entire monitoring area;
determining if the one object is in the predetermined area in the one of the plurality of point clouds;
said analyzing of a subsequent one of the plurality of point clouds is performed only in the predetermined area if the one object in the one point cloud was in the predetermined area.

38. A method for monitoring a patient within a medical monitoring area, the method comprising the steps of:
providing a monitoring system with a depth camera device;
generating a point cloud of the monitoring area with the monitoring system;
analyzing the point cloud for detecting predefined objects;
determining a location of at least one detected object in the monitoring area;
comparing the determined location of the at least one detected object with at least one predefined value for the location of the at least one detected object;
wherein the at least one predefined value for the location of the detected object is formed as an absolute predefined value relative to the monitoring area, wherein the at least one predefined value for the location of the detected object is not defined relative to objects in the monitoring area.

39. A method in accordance with claim 38, wherein:
the at least one absolute predefined value is a location boundary which a patient must not cross;
the steps of the method are carried out only for a section of the monitoring area on a side of the location boundary, on which side the at least one detected object is located.

40. A method in accordance with claim 38, wherein:
the at least one absolute predefined value is a rhythm of the change of the location of the detected object over time.

* * * * *